United States Patent [19]

Landis

[11] 4,269,667
[45] May 26, 1981

[54] ACRYLONITRILE PURIFICATION BY EXTRACTIVE DISTILLATION

[75] Inventor: Norris J. Landis, Cleveland Hts., Ohio

[73] Assignee: Standard Oil Company, Cleveland, Ohio

[21] Appl. No.: 63,216

[22] Filed: Aug. 2, 1979

[51] Int. Cl.³ .............................................. B01D 3/40
[52] U.S. Cl. .................................... 203/76; 203/42; 203/98; 203/DIG. 3; 203/DIG. 19; 260/465.9
[58] Field of Search ............... 203/DIG. 3, 42, 99, 203/91–93, DIG. 19, 95, 96, 97, 83, 79, 76, 85, 39, 98; 260/465.9, 465.3

[56] References Cited

U.S. PATENT DOCUMENTS

| | | | |
|---|---|---|---|
| 2,423,795 | 7/1947 | Patterson | 203/39 |
| 2,791,550 | 5/1957 | West et al. | 203/39 |
| 3,399,120 | 8/1968 | Lovett | 203/85 |
| 3,445,347 | 5/1969 | Borrel et al. | 203/DIG. 3 |
| 3,530,043 | 9/1970 | Horn et al. | 203/DIG. 19 |
| 3,640,852 | 2/1972 | Cupples et al. | 203/39 |
| 3,660,248 | 5/1972 | Tsao | 203/39 |
| 3,852,164 | 12/1974 | Chow | 203/DIG. 19 |
| 3,862,890 | 1/1975 | Presson et al. | 203/DIG. 3 |
| 3,936,360 | 2/1976 | Wu | 203/DIG. 3 |
| 4,039,428 | 8/1977 | Wei | 203/DIG. 19 |
| 4,166,008 | 8/1979 | Wu et al. | 203/DIG. 3 |

Primary Examiner—Wilbur L. Bascomb, Jr.
Attorney, Agent, or Firm—Herbert D. Knudsen; David J. Untener; Larry W. Evans

[57] ABSTRACT

A method for purifying acrylonitrile resulting in capital and operating cost savings consists of distilling a solution of acrylonitrile and impurities in a distillation column under vacuum, and removing the purified acrylonitrile as a vaporous sidestream from the column.

8 Claims, 3 Drawing Figures

ACRYLONITRILE PURIFICATION BY EXTRACTIVE DISTILLATION

BACKGROUND OF THE INVENTION

Acrylonitrile is typically produced by reacting propylene, ammonia and air in the vapor phase over an ammoxidation catalyst. See for example U.S. Pat. Nos. 2,904,580 and 3,890,246. The vaporous reactor effluent from this reaction contains acrylonitrile, acetonitrile, water, HCN, side-reaction products and inert gases. The effluent is usually cooled to a temperature of 90° F. to 230° F. in a quench system to remove unreacted ammonia and various heavy polymers formed or in the reaction.

To recover the acrylonitrile, the prior art has cooled this stream to condense acrylonitrile and/or absorb the acrylonitrile in water in an absorber. The aqueous stream leaving the absorber contains acrylonitrile, acetonitrile, HCN and some impurities.

This aqueous solution then proceeds through various distillation steps to remove the acetonitrile and HCN. The steps can be found in U.S. Pat. No. 3,936,360.

After acetonitrile and HCN have been removed, the prior art then sends this aqueous solution to a drying column to remove water, and to a final product column wherein light and heavy impurities are removed such that specification acrylonitrile product can be obtained. This column operates under a vacuum to decrease polymer formation. Acrylonitrile is removed as a vaporous overhead stream or a liquid sidestream.

The present invention deals with an improved method for separating acrylonitrile from a solution containing acrylonitrile, water and impurities. The purification steps to obtain this solution from the gaseous reactor effluent are not critical, and vary widely. Common to these processing steps, however, is the need for a column to remove water and a final product column for purifying the acrylonitrile.

SUMMARY OF THE INVENTION

The invention is a process for the final purification of acrylonitrile from a solution of acrylonitrile, water and impurities obtained from the recovery and purification of the reactor effluent from the ammoxidation of propylene, comprising feeding said solution to a distillation column, said column operating under a vacuum, and removing purified acrylonitrile as a vaporous sidestream from said column.

The invention may also be stated as a process for the recovery and purification of acrylonitrile produced by the ammoxidation reaction of propylene, molecular oxygen and ammonia which consists of the steps of:
 (a) contacting the ammoxidation reactor effluent with water to absorb the acrylonitrile, acetonitrile, HCN and some impurities, to obtain a first liquid stream containing acrylonitrile;
 (b) extractively distilling said liquid stream to separate the acrylonitrile from the acetonitrile to obtain a second stream of acrylonitrile, water, HCN and impurities;
 (c) distilling said second stream to separate the acrylonitrile from the HCN to obtain a solution of acrylonitrile, water and some impurities, the improvement comprising;
 (d) distilling said solution under vacuum, and removing a vaporous sidestream of purified acrylonitrile.

The present invention, by eliminating the separate drying column, thus achieves in one column what the prior art accomplished in two separate columns. This results in substantial capital and operating cost savings to the process.

The steps necessary to obtain the solution of acrylonitrile, water and impurities vary widely. See for example, U.S. Pat. No. 3,399,120. This particular reference discloses a method for separating acetonitrile from the absorber bottoms stream using extractive distillation with water. In such processes, the acrylonitrile, water and HCN are removed as an overhead stream from the extractive distillation column. The present invention is concerned with such a stream after the HCN has been removed.

The removal of HCN is typically accomplished in a distillation column wherein HCN is removed overhead in vapor form, and acrylonitrile and water are recovered as a bottoms stream.

Certain impurities such as propionitrile are produced from side reactions during the primary conversion of propylene to acrylonitrile. Other impurities such as polymers are produced during the recovery and purification steps described above. Many of these impurities follow or tend to follow the acrylonitrile through the processing steps of removing acetonitrile and HCN.

These impurities can have a harmful effect on the end uses for acrylonitrile. British Pat. No. 1,131,134 describes an impurity known as oxazole and its effects on acrylonitrile polymers.

Prior art methods of removing water and these remaining impurities from acrylonitrile have been by the use of two columns; a drying column to remove water and a product column to remove the remaining impurities. The drying column has been combined with the HCN distillation column to achieve the removal of both water and HCN in a single column.

The product column of the prior art has been operated under a vacuum so that lower temperatures can be used and thus prevent formation of more polymers. The feed to this prior art column usually enters well below the midpoint.

Acrylonitrile has been removed from this product column in one of two ways. First, acrylonitrile has been removed as a vaporous overhead stream. This method has certain disadvantages in that any impurities contained in the feed that boil lower than acrylonitrile are not removed.

A second method of recovering acrylonitrile has been to remove a liquid sidestream, usually very close to the top tray. This of course allows the lower boiling impurities to be be removed from the column as a vaporous overhead stream without greatly contaminating the product acrylonitrile.

In the practice of the present invention, however, it has been found that a single column can be used to both remove water and obtain a purified acrylonitrile product. This column, like the prior art, operates under a vacuum. It has been discovered that by feeding the solution of acrylonitrile, water and impurities to the uppermost trays of this column, and by removing a vaporous sidestream from between the tenth and thirtieth tray from the bottom of this column, acrylonitrile can be recovered with an acceptable water content and essentially free of impurities.

DESCRIPTION OF THE DRAWINGS

Referring to FIG. 1, a gaseous reactor effluent containing acrylonitrile, produced from the catalytic ammoxidation of propylene enters quench column 102 through line 100. A quench liquid, usually water, enters the column through line 104 thereby cooling the reactor effluent and removing various heavy polymers. The pH of this quench liquid may be controlled in order to remove any unreacted ammonia. The quench liquid containing polymers is removed from the quench column through line 106 and passes to waste disposal.

The cooled reactor effluent gases leave the quench column through line 108 and pass to absorber 110. Water enters the absorber through line 112 and passes countercurrently to the gas. Inert gases and unreacted feed exit the absorber in vaporous form through line 114, while an aqueous solution of acrylonitrile, acetonitrile, HCN and impurities leaves the absorber bottoms through line 116 and is sent to recovery column 118.

In the recovery column, water is again used through line 120 to extractively distill the acrylonitrile. Acetonitrile with some minor amount of acrylonitrile leaves the recovery column through line 122. This stream can be sent to an additional purification step for recovery of the acetonitrile.

Acrylonitrile, HCN and water leave the recovery column through line 124 and pass to the HCN column 126. Here the stream is distilled such that HCN is remove overhead as a vapor through line 128 and the acrylonitrile and water removed as a bottoms stream through line 130.

This aqueous solution of acrylonitrile, water and some impurities is then passed to a drying column 132. Distillation is then performed such that water exits overhead through line 134 and the partially dried acrylonitrile and impurities leave the bottom of the column through line 136.

This stream is then sent to product column 138 for final purification. The lower boiling impurities leave the product column through line 140 as an overhead vapor. The heavier boiling impurities exit the product column through line 142 and are typically passed back to the quench system or to waste disposal. A liquid sidestream of specification acrylonitrile is removed from the product column through line 144 and sent to storage.

Figure 1:
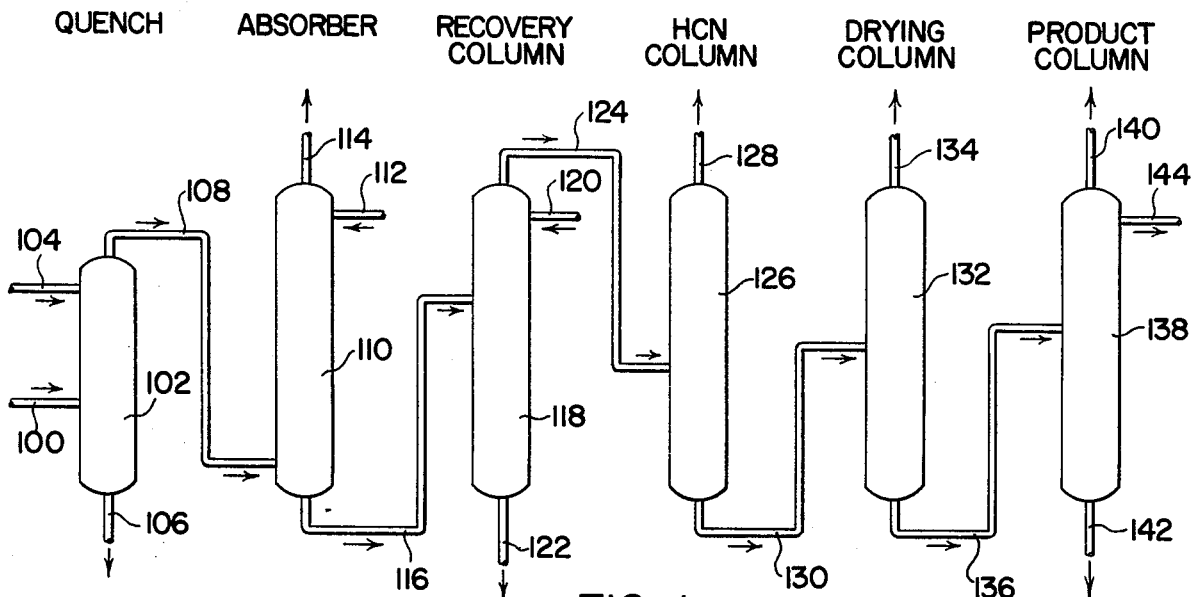
FIG. 1 shows a prior art method for purifying acrylonitrile.
Figure 2:
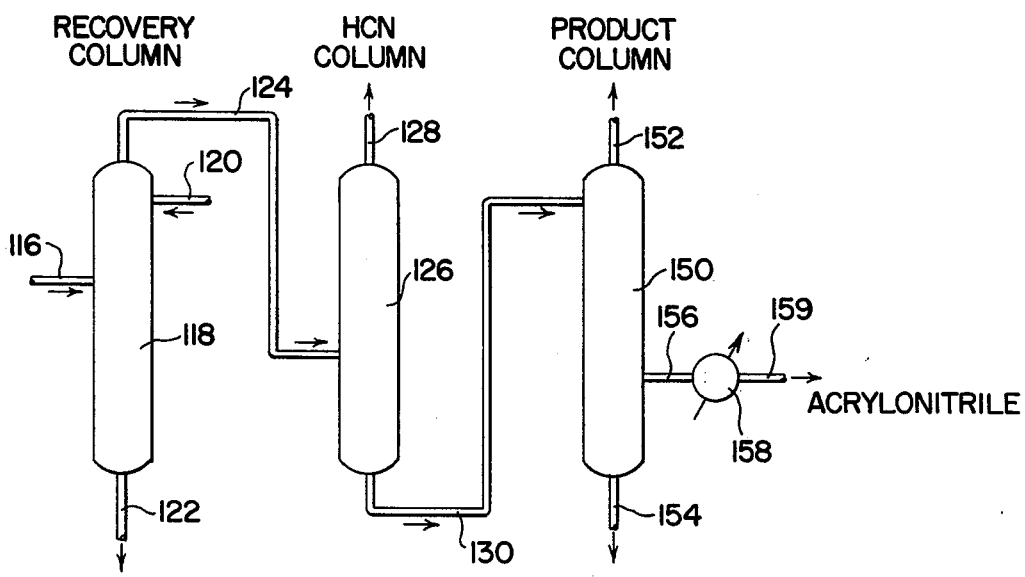
FIG. 2 shows an embodiment of the present invention as applied to the process of FIG. 1.

FIG. 2 shows an embodiment of the present invention as applied to the prior art process of FIG. 1. As discussed above, an aqueous solution of acrylonitrile, water and some impurities leave the HCN column 126 through line 130. Instead of being sent to a drying column as in FIG. 1, this stream is passed to the invention's product column 150. Here the stream preferably enters on the top tray of the product column. Heat is supplied to the product column to perform distillation. Lower boiling impurities exit as a vapor through line 152 and the heavier impurities leave the product column bottom through line 154. A vaporous sidestream 156 is removed from product column 150 in the lower half of the product column. This stream is then condensed in indirect condenser 158, and a liquid specification acrylonitrile product is sent through line 159 to storage.

Figure 3:
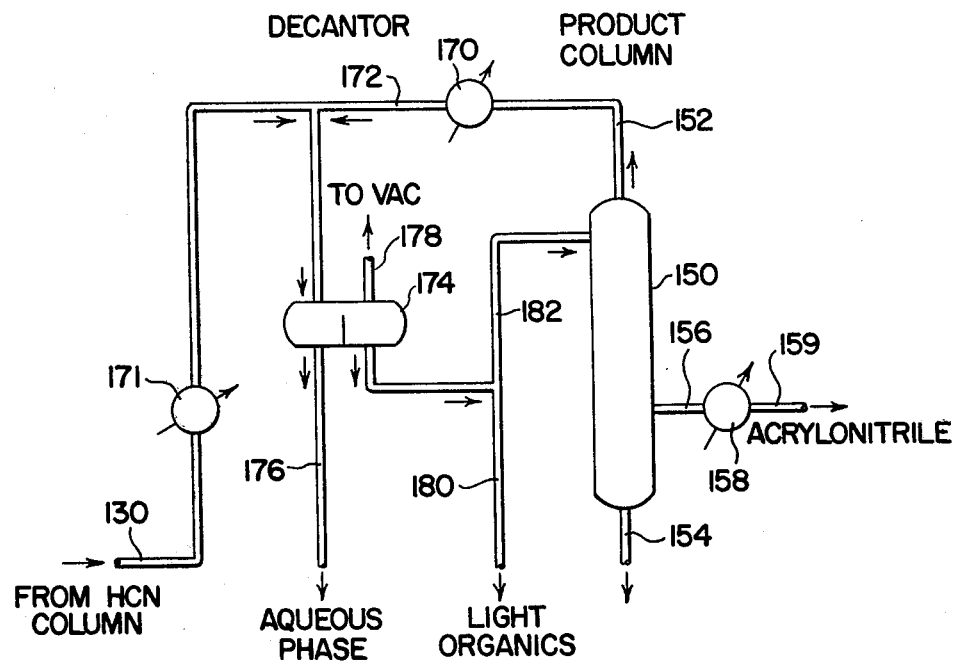
FIG. 3 describes a preferred embodiment of FIG. 2 wherein a decanter is used on the feed and overhead streams of the product column.

FIG. 3 shows the use of a purification decanter to remove water from the feed and the overhead stream of the product column. Bottoms stream 130 from the HCN column containing acrylonitrile, water and impurities, is cooled in exchanger 171 and is sent to decanter 174. Also being fed to this decanter is overhead stream 172 from the product column which may be combined with stream 130 or separately fed to the decanter.

In decanter 174, two phases are formed. The heavier aqueous phase is removed from the decanter through line 176 and can be used as recycle water for the process. The lighter organic phase containing acrylonitrile, some water and impurities is separated from the aqueous phase in the decanter through the use of a weir. This organic phase leaves the decanter and is passed as feed to the product column through line 182. Also shown in this figure is the removal of a small amount of this phase through line 180 to prevent a build-up of the lighter impurities.

The vacuum operation for the product column may be accomplished by pulling a vapor stream 178 from decanter 174. The overhead vapors 152 from the product column 150 proceed to condenser 170. Here the vapors are partially condensed and passed through line 172 to the decanter. The remaining operation of the product column is identical to FIG. 2. Use of this decanter allows the removal of water from both the feed and the overhead streams, and also allows the recovery of any acrylonitrile that may exit through the overhead of the product column.

The feed to the invention's product column contains acrylonitrile, water, the impurities mentioned previously, and traces of HCN and acetonitrile. Small amounts of HCN and acetonitrile are found in this stream because 100% separation of these components is not totally feasible.

The product column of the present invention is a distillation column having distillation trays. The exact number of trays will of course depend on the relative composition of acrylonitrile and water found in the feed. It is preferred that the product column have about 30 to 60 trays.

Unlike the prior art, the feed to this column should enter above the sidestream removal point. It is preferred that this feed enter the upper quarter of the column. Most preferred as a feed tray is the top tray of the column.

Also preferred is the use of a decanter on the feed and overhead streams as shown in FIG. 3. This allows for a more efficient removal of water and impurities.

The product column should operate under vacuum conditions so that a minimum of polymer formation takes place, thus minimizing fouling. This vacuum should be between 2 and 10 psia at the top tray. Preferred is a vacuum between 3 and 8 psia, with 5 to 6 psia being most preferred.

With the feed on the top tray, the liquid and vapor compositions become leaner in components more volatile than acrylonitrile in successive stages from the top. Likewise, there is increasing vaporization in components heavier than acrylonitrile in the same manner. The location of the sidestream removal should be such that both light and heavy impurities are minimized. This point is normally found in the lower half of the column. For example, a column of 35 trays with the feed on the 35th tray may have a vapor sidestream removal just above tray 10.

A method for determining the location of this vaporous draw is by computer modeling the column using the various components anticipated in the feed. This will give an approximate location that may then be bracketed with multiple draw-off points above and below this tray. Such computer programs for performing such calculations are well known and practiced in the design of distillation columns.

After removal, the vaporous sidestream can then be condensed in an indirect heat exchanger and sent to storage.

The net overhead of the column, containing the lighter impurities, can be recycled back to the recovery column. The bottoms stream containing the heavier impurities can be sent to waste disposal or returned to the quench system as shown in U.S. Pat. No. 3,936,360.

As in the prior art, it may be desirable to add acrylonitrile polymer inhibitor to the product column to minimize polymerization. Such an inhibitor, however, is not a necessary or critical aspect of the invention. The invention is illustrated by the following Example.

EXAMPLE

Separation of Water and Impurities from Acrylonitrile

A feed stream of acrylonitrile, 3% water, 285 ppm HCN, 40 ppm acetonitrile, and approximately 1200 ppm of various impurities such as acetone and propionitrile was fed at a rate of 102 cc/min. to the invention's product column.

This column consisted of a 45 tray 50 mm diameter Oldershaw Column. The feed entered the column on the 45th tray.

A vacuum of 15–16 inches Hg was maintained on the column using a water sealed vacuum pump. Indirect heat exchange was used to provide the heat necessary for distillation. The temperature of the vapors leaving the overhead was 105° F. with a bottom temperature of 155° F.

A vapor sidestream was removed from the column above the 10th tray. This stream was condensed and analyzed for its water, HCN and impurities content. All of the water and more than 90% of the HCN had been removed. The concentration of the other various impurities were equal to or lower than concentrations found in acrylonitrile product streams purified by prior art methods.

We claim:

1. A process for the recovery and purification of acrylonitrile produced by the ammoxidation reaction of propylene, molecular oxygen and ammonia which consists of the steps of:
   (a) contacting the gaseous ammoxidation reactor effluent with water to absorb the acrylonitrile, acetonitrile, HCN and some impurities, and to obtain a first liquid stream containing acrylonitrile;
   (b) extractively distilling with water in a distillation column said first liquid stream to separate the acrylonitrile from the acetonitrile and to obtain a overhead stream of acrylonitrile, water, HCN and impurities;
   (c) distilling in a distillation column said overhead stream of (b) to separate the acrylonitrile from the HCN to obtain a bottoms solution of acrylonitrile, water and some impurities, the improvement comprising;
   (d) distilling said solution in a distillation column under vacuum, and removing a vaporous sidestream of purified acrylonitrile.

2. The process of claim 1 wherein the solution of step (d) is distilled in a distillation column having between 30 and 60 trays.

3. The process of claim 2 wherein the solution is fed to the topmost tray of the column.

4. The process of claim 2 wherein the vaporous sidestream is removed below the feed tray.

5. The process of claim 2 wherein the vaporous sidestream is removed from the lower two-thirds of the column.

6. The process of claim 4 wherein the vaporous sidestream removed is condensed using indirect heat exchange.

7. The process of claim 1 wherein said solution of step (c) is passed to a decanter to separate an aqueous phase and an organic phase, and feeding said organic phase to said distillation column of step (d).

8. The process of claim 7 wherein an overhead vapor stream is removed from said distillation column of step (d), at least partially condensed, and passed to said decanter.

* * * * *